US012727887B2

(12) United States Patent
Fleury et al.

(10) Patent No.: US 12,727,887 B2
(45) Date of Patent: Sep. 8, 2026

(54) ANASTOMOSIS DEVICE, SYSTEMS, AND METHODS

(71) Applicant: BOSTON SCIENTIFIC SCIMED, INC., Maple Grove, MN (US)

(72) Inventors: Sean P. Fleury, Princeton, MA (US); John Thomas Favreau, Spencer, MA (US); James J. Scutti, Norwell, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 370 days.

(21) Appl. No.: 17/740,332

(22) Filed: May 9, 2022

(65) Prior Publication Data

US 2022/0354504 A1 Nov. 10, 2022

Related U.S. Application Data

(60) Provisional application No. 63/186,338, filed on May 10, 2021.

(51) Int. Cl.

| | |
|---|---|
| ***A61B 17/12*** | (2006.01) |
| ***A61B 17/11*** | (2006.01) |
| *A61B 17/00* | (2006.01) |

(52) U.S. Cl.

CPC .................. *A61B 17/12045* (2013.01); *A61B 2017/00477* (2013.01); *A61B 2017/00867* (2013.01); *A61B 17/11* (2013.01); *A61B 2017/1107* (2013.01); *A61B 17/1114* (2013.01); *A61B 2017/1132* (2013.01); *A61B 2017/1139* (2013.01); *A61B 17/1214* (2013.01); *A61B 17/12145* (2013.01)

(58) Field of Classification Search

CPC .... A61B 17/12045; A61B 2017/00477; A61B 2017/00867; A61B 2017/1139; A61B 17/11; A61B 17/1114; A61B 17/1214; A61B 17/12145; A61B 2017/1132; A61B 2017/1107

See application file for complete search history.

(56) References Cited

U.S. PATENT DOCUMENTS 5,540,701 A * 7/1996 Sharkey ................ A61B 17/11 606/198

2002/0029048 A1 3/2002 Miller (Continued)

FOREIGN PATENT DOCUMENTS

| | | |
|---|---|---|
| JP | 2009066408 A | 4/2009 |
| JP | 2017515631 A | 6/2017 |
| WO | 2019217851 A1 | 11/2019 |

OTHER PUBLICATIONS

Invitation to Pay Additional Fees dated Aug. 18, 2022 for International Application No. PCT/US2022/028399.

*Primary Examiner* — Jing Rui Ou

(74) *Attorney, Agent, or Firm* — Seager, Tufte & Wickhem, LLP

(57) ABSTRACT

The present application relates to medical devices for establishing an anastomosis between body lumens. In one example, an elongate member is configured to move between a first configuration and a second configuration. The elongate member may comprise a first end, a second end, and a middle segment extending therebetween. In the second configuration, each of the first and second ends may bend towards a center plane of the middle segment in a bent back end and form one or more loops.

17 Claims, 6 Drawing Sheets

(56) References Cited

U.S. PATENT DOCUMENTS

| | | | | |
|---|---|---|---|---|
| 2002/0065524 | A1* | 5/2002 | Miller | A61B 17/068 606/139 |
| 2003/0040804 | A1 | 2/2003 | Stack et al. | |
| 2003/0225420 | A1* | 12/2003 | Wardle | A61B 17/068 606/151 |
| 2004/0073237 | A1 | 4/2004 | Leinsing | |
| 2005/0143763 | A1* | 6/2005 | Ortiz | A61B 17/1114 606/153 |
| 2006/0052821 | A1 | 3/2006 | Abbott et al. | |
| 2008/0208214 | A1* | 8/2008 | Sato | A61B 17/1114 606/139 |
| 2013/0150869 | A1 | 6/2013 | Conklin et al. | |
| 2014/0222040 | A1 | 8/2014 | Park et al. | |
| 2015/0313599 | A1 | 11/2015 | Johnson et al. | |
| 2017/0086824 | A1 | 3/2017 | Khan | |
| 2018/0271530 | A1* | 9/2018 | Dayton | A61F 2/95 |
| 2020/0268537 | A1 | 8/2020 | Reisin et al. | |
| 2021/0059659 | A1 | 3/2021 | Dayton et al. | |
| 2021/0236129 | A1 | 8/2021 | Topazian | |
| 2022/0354504 | A1 | 11/2022 | Fleury et al. | |

* cited by examiner

ANASTOMOSIS DEVICE, SYSTEMS, AND METHODS

CROSS-REFERENCE TO RELATED APPLICATIONS

This application claims the benefit of priority of U.S. Provisional Application No. 63/186,338, filed May 10, 2021, the entire disclosure of which is hereby incorporated by reference herein for all purposes.

FIELD

The present disclosure relates generally to the field of medical devices. In particular, the present disclosure relates to medical devices for establishing a path between adjacent body lumens, such as an anastomosis device which holds tissue layers of adjacent body lumens together.

BACKGROUND

Placement of devices such as self-expanding stents (e.g., self-expanding metal stent or SEMS) within an anatomical area (e.g., body lumen, passage, vessel, duct, etc.) may enable fluid communication from one area to another. For example, a stent may enable flow of material from one body lumen to another.

However, devices such as stents may carry various disadvantages. For example, stents may be expensive to manufacture, and/or may require highly specialized systems and methods of delivery such as specialized systems of sheaths comprising lumens wide enough to carry the stent.

Accordingly, a variety of advantageous medical outcomes may be realized by the devices and/or methods of the present disclosure.

SUMMARY

In an aspect of the present disclosure, an anastomosis device may comprise an elongate member configured to move between a first configuration and a second configuration. The elongate member may comprise a first segment, a second segment, and a middle segment extending therebetween. In the second configuration, each of the first segment and the second segment may extend towards the middle segment to form a bent back end of the device. Each of the first segment and the second segment may form one or more loops in the second configuration.

In the above aspect, the elongate member in the first configuration may be substantially straight along a lateral axis extending along the middle segment.

The elongate member may be a wire.

For one or each of the first segment and the second segment, the bent back end may be along a portion of the elongate member between the middle segment and the one or more loops.

The elongate member may have a non-circular cross section. The elongate member may have a non-circular cross section along a full length thereof. The elongate member may have a non-circular cross section along a partial length thereof.

The one or more loops may be configured to appose respective first and second tissue layers through which the middle segment extends. The one or more loops may be configured to draw the first and second tissue layers into apposition.

The anastomosis device may comprise at least one elongate member end extending towards the middle segment.

The middle segment may be offset from a central axis extending through the one or more loops.

The first segment, the second segment, or both may comprise at least one anchor feature.

The one or more loops may be in a plane transverse to an axis defined by the middle segment.

The one or more loops may define an anastomosis region. The middle segment may not extend through a center of the anastomosis region. The bent back end may be configured to be grasped by a grasper while disposed in tissue.

In another aspect of the present disclosure, a method of creating an anastomosis may comprise advancing a sheath through first and second tissues. The sheath may contain an elongate body configured to transition between a first configuration and a second configuration. The method may include deploying a distal end of the elongate body distally to the second tissue such that the distal end of the elongate body forms at least one distal circumferential loop in the second configuration. The method may include proximally retracting the sheath with the distal circumferential loop such that the at least one distal loop engages the second tissue. The method may include proximally retracting the sheath with respect to the elongate body to deploy a proximal end of the elongate body. The proximal end of the elongate body may, in the second configuration, form at least one proximal circumferential loop such that the at least one proximal loop engages the first tissue wall. The method may include excising a section of each of the first and second tissues between the at least one distal loop and the at least one proximal loop. The tissue may be in an anastomosis region circumscribed by the at least one distal loop and the at least one proximal loop.

In at least the above aspect, the elongate body may bend towards the second tissue to form a distal bent back end. The elongate body may bend towards the first tissue to form a proximal bent back end.

Deploying the distal end of the elongate body may include proximally retracting the sheath with respect to the elongate body, distally advancing the elongate body with respect to the sheath, or both.

Deploying the distal end of the elongate body may include uncovering the distal end such that the elongate body bends towards the second tissue to form a distal bent back end. Deploying the proximal end of the elongate body may comprise uncovering the proximal end such that the elongate body bends towards the first tissue to form a proximal bent back end.

The elongate body in the second configuration may comprise a substantially straight middle segment extending between the at least one proximal circumferential loop and the at least one distal circumferential loop. The substantially straight middle segment may be off-centered from a central axis extending through the elongate body in the second configuration. The method may further include excising the tissue without interference of the middle section.

The elongate body in the first configuration may be a substantially straight wire.

The at least one or more loops may be configured to draw the first and second tissue layers into apposition.

In an additional aspect of the present disclosure, an anastomosis device may comprise an elongate member configured to transition between a first configuration and a second configuration. In the first configuration, the elongate member may be substantially straight. In the second configuration, the anastomosis device may comprise a first retention member, a second retention member, and a middle segment extending therebetween. In the second configuration, each of the first segment and the second segment may extend towards the middle section to form a respective first and second bent back end of the device. In the second configuration, each of the first segment and the second segment may form a respective retention member. The first bent back end may be positioned along the elongate member between the first retention member and the middle segment. The second bent back end may be positioned along the elongate member between the second retention member and the middle segment. The retention members may be in the form of loops.

In the above and various aspects, the first retention member and the second retention member may be configured to appose first and second tissue layers. The retention members may be configured to draw the first and second tissue layers into apposition.

The first retention member, the second retention member, or both may comprise one or more circumferential loops. The one or more circumferential loops may define or circumscribe an anastomosis region extending longitudinally therebetween.

The middle segment may not intersect a central region of the anastomosis region. The middle segment may be offset from the central region of the anastomosis region, and may extend along a periphery of the anastomosis region.

The elongate member may have a non-circular cross section.

At least one end of the elongate member may extend towards the middle segment.

The middle segment may not be centered within a region defined by the first retention member, or the second retention member, or both.

In accordance with various principles of the present disclosure, an anastomosis device may comprise an elongate member configured to move between a first configuration and a second configuration. The elongate member may comprise a first segment, a second segment, and a middle segment extending therebetween. In the second configuration, each of the first segment and the second segment may extend toward the middle segment to form a bent back end of the device and form one or more loops.

The elongate member, in the first configuration, may be a substantially straight wire, with the first and second segments extending substantially coaxially from the middle segment.

The bent back ends of the device may extend from the middle segment to the one or more loops.

In another aspect, a method of creating an anastomosis may comprise advancing a sheath through first and second tissues, the sheath containing an elongate body configured to transition between a first configuration and a second configuration. The method may include deploying a distal end of the elongate body distally to the second tissue such that the distal end of the elongate body forms at least one distal circumferential loop in the second configuration. The method may include proximally retracting the sheath with the distal circumferential loop such that the at least one distal loop engages the second tissue. The method may include proximally retracting the sheath with respect to the elongate body to deploy a proximal end of the elongate body. The proximal end of the elongate body, in the second configuration, may form at least one proximal circumferential loop such that the at least one proximal loop engages the first tissue wall. The method may include excising a section of each of the first and second tissues in an anastomosis region circumscribed by the at least one distal loop and the at least one proximal loop.

In the above and other aspects, deploying the distal end of the elongate body may comprise uncovering the distal end such that the elongate body bends towards the second tissue to form a distal bent back end. Deploying the proximal end of the elongate body may comprise uncovering the proximal end such that the elongate body bends towards the first tissue to form a proximal bent back end.

In the above and other aspects, the elongate body in the second configuration may comprise a substantially straight middle segment extending between the at least one proximal circumferential loop and the at least one distal circumferential loop. The substantially straight middle segment may be off-centered from a central axis extending through the elongate body in the second configuration. The method may further comprise excising the tissue without interference of the middle section.

In an additional aspect, an anastomosis device may comprise an elongate member configured to transition between a first configuration and a second configuration. In the first configuration, the elongate member may be substantially straight. In the first configuration, the first and second segments may extend substantially coaxially from the middle segment. In the second configuration, the elongate member may form a first retention member, a second retention member, and a middle segment extending therebetween. A first bent back end may extend from the middle segment and towards the middle segment to form the first retention member. A second bent back end may extend from the middle segment and towards the middle segment to form the second retention member.

In the above and other aspects, the first retention member and the second retention member may be configured to appose first and second tissue layers. The first and second retention members may be configured to draw the first and second tissue layers into apposition. The first retention member, the second retention member, or both may comprise one or more circumferential loops. The one or more circumferential loops may define an anastomosis region extending longitudinally therebetween.

The middle segment may not intersect a central region of the anastomosis region. The middle segment may be offset from the central region of the anastomosis region, and may extend along a periphery of the anastomosis region.

The elongate member may have a non-circular cross section.

The middle segment may not be not centered within a clamping region defined by the first retention member, or the second retention member, or both.

In yet another aspect, an anastomosis device may comprise an elongate member configured to transition between a first configuration and a second configuration. In the first configuration, the elongate member may be substantially straight. In the second configuration, the elongate member may form a first retention member, a second retention member, and a middle segment extending therebetween. The middle segment may be offset from a central region of an area circumscribed by the first and second retention members. The central region may have a sufficiently large diameter for an excision of tissue extending longitudinally therethrough to create a port extending through the anastomosis device.

In the above and other aspects, the first retention member and the second retention member may be configured to appose first and second tissue layers. The first and second retention members may be configured to draw the first and second tissue layers into apposition. The first retention member, the second retention member, or both may comprise one or more circumferential loops.

In the second configuration of the device, a bent back end of the device may be defined between the middle segment and at least one of the retention members.

The middle segment may not intersect a central region of the anastomosis region. The middle segment may be offset from the central region of the anastomosis region, and may extend along a periphery of the anastomosis region.

The elongate member may have a non-circular cross section.

The middle segment may not be not centered within a region defined by the first retention member, or the second retention member, or both.

According to one or more aspects of the present disclosure, an anastomosis device may comprise an elongate member configured to move between a first configuration and a second configuration. The elongate member may comprise a first segment, a second segment, and a middle segment extending therebetween. In the second configuration, either or each of the first segment and the second segment extends toward the middle segment to form a respective first and second bent back end of the device and to form a respective retention member.

In the above and other aspects, the elongate member in the first configuration may be substantially straight.

The first and/or second segment may extend substantially coaxially from the middle segment.

Each of the first segment and the second segment may form the respective bent back ends of the device along a portion of the elongate member between the middle segment of the elongate member and the respective retention member.

The elongate member may have a non-circular cross section, and may have a non-circular cross section along a partial or full length thereof.

The retention members may be configured to appose respective first and second tissue layers through which the middle segment extends. The retention members may be configured to draw the first and second tissue layers into apposition.

The anastomosis device may further comprise at least one elongate member free end extending towards the middle segment.

The middle segment may be offset from a central axis extending through the one or more retention members.

The first segment, the second segment, or both may comprise at least one anchor feature.

The retention members may be in a plane transverse to an axis defined by the middle segment.

The retention members may form one or more loops circumscribing an anastomosis region. The middle segment may not intersect a central region of the anastomosis region.

In another aspect of the present disclosure, an anastomosis device may comprise an elongate member configured to transition between a first configuration and a second configuration. In the first configuration, the elongate member may be substantially straight. In the second configuration, the elongate member may form a first retention member and a second retention member with a middle segment extending therebetween. The middle segment may be offset from a central region of an area circumscribed by the first and second retention members. The central region may have a sufficiently large diameter for an excision of tissue extending longitudinally therethrough to create a port extending through the anastomosis device.

In the above and other aspects, the first retention member and the second retention member may be configured to appose first and second tissue layers. The first and second retention members may be configured to draw the first and second tissue layers into apposition.

The first retention member, the second retention member, or both may comprise one or more circumferential loops.

In the second configuration, a bent back end of the device may be defined between the middle segment and at least one of the first retention member or second retention member.

The middle segment may not extend through a central region of the anastomosis region.

The elongate member may have a non-circular cross section.

The middle segment may not be centered within a clamping region defined by the first retention member, or the second retention member, or both, and may be outside the anastomosis region.

Other technical features may be readily apparent to one skilled in the art from the following figures, descriptions, and claims.

BRIEF DESCRIPTION OF THE SEVERAL VIEWS OF THE DRAWINGS

Non-limiting examples of the present disclosure are described with reference to the accompanying figures, which are schematic and not intended to be drawn to scale. In the figures, each identical or nearly identical component illustrated is typically represented by a single numeral. For purposes of clarity, not every component is labeled in every figure, nor is every component in each embodiment of the disclosure shown where illustration is not necessary to allow those of skill in the art to understand the disclosure. In the figures.

DETAILED DESCRIPTION

Figure 1A:
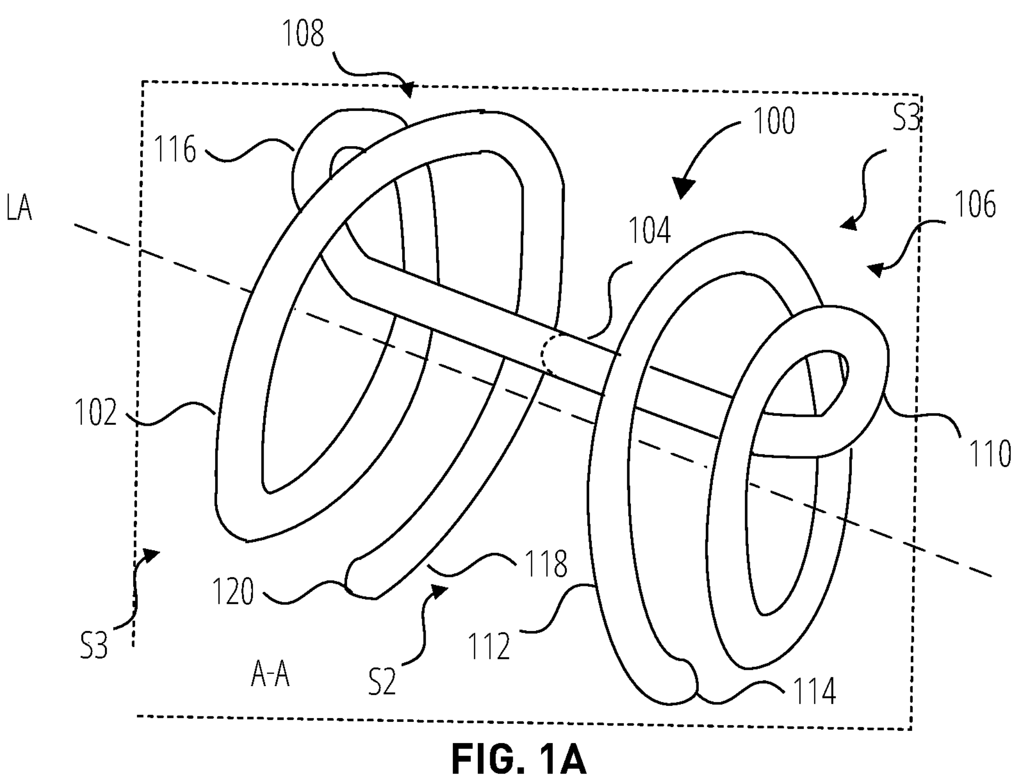
FIG. 1A illustrates an orthogonal view of an anastomosis device according to one or more embodiments described herein.

The present disclosure is not limited to the particular embodiments described. The terminology used herein is for the purpose of describing particular embodiments only and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure may be described with specific reference to medical devices (e.g., anastomosis devices, tissue clamps, etc.) and systems for drainage of the gallbladder, pseudocysts, and/or for a gastrojejunostomy, or the like, it should be appreciated that such medical devices may be used in a variety of medical procedures (e.g., external biliary drain conversion, enteroenterostomy, gastroduodenostomy and gastroileostomy, etc.) to establish and/or maintain a temporary or permanent open flow or drainage passage from or between a variety of body organs, lumens, ducts, vessels, fistulas, cysts and spaces (e.g., the dermis, stomach, duodenum, jejunum, small intestine, gallbladder, kidneys, pancreas, biliary/pancreatic trees, bladder, ureter, abscesses, walled-off pancreatic necrosis (WOPN), bile ducts, etc.). The devices may be inserted via different access points and approaches, e.g., percutaneously, endoscopically, laparoscopically or some combination thereof. The medical devices disclosed herein are formed of shape memory material and may automatically assume a preset shape, but in other embodiments the medical device may be shapeable by other means, including, e.g., a manual manipulation with a grasper, heating with an electric element, or the like. Moreover, such medical devices are not limited to drainage, but may facilitate access to organs, vessels or body lumens for other purposes, such as creating a path to divert or bypass fluids or solids from one location to another, removing obstructions and/or delivering therapy, including non-invasive or minimally invasive manipulation of the tissue within the organ and/or the introduction of pharmacological agents via the open flow passage.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

As used herein, "proximal" refers to the direction or location closest to the user (medical professional or clinician or technician or operator or physician, etc., such terms being used interchangeably herein without intent to limit, and including automated controller systems or otherwise), etc., such as when using a device (e.g., introducing the device into a patient, or during implantation, positioning, or delivery), and "distal" refers to the direction or location furthest from the user, such as when using the device (e.g., introducing the device into a patient, or during implantation, positioning, or delivery). "Longitudinal" means extending along the longer or larger dimension of an element. "Central" means at least generally bisecting a center point and/or generally equidistant from a periphery or boundary, and a "central axis" means, with respect to an opening, a line that at least generally bisects a center point or region of the opening, extending longitudinally along the length of the opening when the opening comprises, for example, a circumscribed region, a tubular element, a channel, a cavity, or a bore.

Various aspects of the present disclosure maybe described with respect to one or more body lumens. It will be understood that alternatively, or additionally, a body lumen may refer to a body cavity. For example, a body lumen may be an intestine, a stomach, a body of a cyst, a peritoneal cavity, or the like.

In various embodiments of the present disclosure, a medical device (e.g., anastomosis device, tissue clamp, port device, or the like) may be configured to extend between first and second body lumens and/or across first and second body tissues and assist with apposing or maintaining apposition of respective layers (e.g., muscularis layers) of apposed body tissue. Maintenance of apposed tissue (such as of apposed body lumens) in apposition allows a temporary, long term, or permanent open flow, port, or access passage to be formed therebetween. For the sake of convenience and without intent to limit, an open flow, port, or access passage may be referenced herein as an anastomosis for the sake of convenience and without intent to limit. Likewise, medical devices of the present disclosure may be collectively referred to as "anastomosis devices" for the sake of convenience and without intent to limit.

Traditional anastomosis devices may be formed of solid materials and/or one or multiple wires configured to form 3-dimensional shapes, which may have expanded and unexpanded configurations such that they may be delivered in an unexpanded configuration and deployed to transition to an expanded configuration. However, even in unexpanded configurations, traditional devices may have relatively bulky shapes, such as tubular configurations, which may require specialized delivery systems. For example, traditional devices may be delivered with one or more sheaths defining lumens wide enough to carry the respective device.

Due to their complex and often bulky methods of delivery, certain anatomical areas may be difficult to access or may be substantially inaccessible for treatment with traditional devices. For example, highly tortuous and/or narrow passages of body lumens may be difficult or impossible to navigate endoscopically with existing delivery systems.

Even when deployed, traditional devices may present one or more disadvantages. For example, stents may maintain a high ratio of outer surface contact with apposed tissue, for example, in order to reduce risk of migration. However, contact with tissue may cause undesired irritation to the tissue, resulting in discomfort and/or risk of infection for a patient. Various anastomosis devices may comprise coverings (i.e., silicone coverings extended over mesh structures) in order to reduce trauma to apposed tissue. However, covered devices may be prone to migration, potentially leading to pain for a patient and/or additional procedure(s) in order to reposition a device.

Furthermore, traditional devices and/or their delivery systems may be expensive to manufacture, thereby reducing their access by healthcare professionals and/or systems.

One or more of these concerns may be addressed by devices, systems, and/or methods of the present disclosure.

In at least one example of the present disclosure, an anastomosis device may be formed with a single elongate body or member, such as a wire, which may have a delivery configuration and a deployed configuration. In the delivery configuration, various devices according to the present disclosure may be configured as a single elongate member, which need not be a tubular member, such as an extended wire. The single elongate member may comprise a substantially uniform diameter.

Delivery of various devices of the present disclosure may be facilitated by one or more sheaths which need only define lumens with inner diameters sufficient to carry the extended elongate body (e.g., a single wire). Delivery sheaths of the present disclosure may thus be narrower than delivery sheaths used with traditional anastomosis devices. Accordingly, some embodiments of the present disclosure may enable access to and treatment of more remote anatomical regions than traditional systems. For example, devices of the present disclosure may be configured to access and/or treat anatomical areas accessible only via a device having a diameter which may be as small as a guidewire.

According to various embodiments of the present disclosure, anastomosis devices may be configured to extend across tissue layers with a single wire (i.e., elongate member). The element from which the elongate member is formed may be compact during delivered as well as once deployed, without itself expanding. Instead, the elongate member may transition or shift configurations from a first delivery configuration (e.g., elongated to facilitate delivery) to a second configuration once deployed (e.g., configured to contact the surface of at least one tissue such as to be held in place with respect to the at least one tissue). In the second configuration, the elongate member may be configured to include one or more retention members which may contact a tissue surface, such as on either side of apposed tissues.

More particularly, in the first configuration, the element from which the elongate member is formed may be elongated (e.g., substantially straight), whereas in the second configuration the element from which the elongate member is formed may bend along different segments of the elongate member, so that such segments extend transverse to a longitudinal axis of the device. For instance, the elongate member may comprise a first segment or portion, a second segment or portion, and a middle segment or portion between the first and second segments. The first segment and/or the second segment of the elongate member may bend to form retention members when the elongate member is in the second configuration. A first retention member may be formed along the first segment (such as by the first segment bending to form a retention member), and a second retention member may be formed along the second segment (such as by the second segment bending to form a retention member). The retention members may extend generally transverse to the longitudinal axis of the anastomosis device to contact tissue across which the anastomosis device extends to form an anastomosis therethrough.

In some embodiments, in the second configuration of the elongate member, at least one of the first segment or the second segment (which generally extend away from the middle segment when the elongate member is in an elongated first configuration) may be bent towards the middle segment to define a bent end of the device. The bent end of the device is distinguished from the end of the elongate member forming the device, and is defined along a portion of the elongate member between the middle segment and the first or second segment forming the bent segment. For instance, the first segment may have a first end along or adjacent a first free end of the elongate member and a second end along or adjacent the middle segment. Similarly, the second segment may have a first end along or adjacent a second free end of the elongate member and a second end along or adjacent the middle segment. The first segment of the elongate member may be bent such that the distance between the first segment first end and the second segment first end is shorter than the distance between the first segment second end and the second segment first end. Such bend of the first segment may be considered to form a first end of the anastomosis device. The second segment of the elongate member may be bent such that the distance between the second segment first end and the first segment first end is shorter than the distance between the second segment second end and the first segment first end. Such bend of the second segment may be considered to form a second end of the anastomosis device. In embodiments in which a segment is bent such that the distance of the first end (adjacent a free end of the elongate member) of one of the segments to the other segment is shorter than the distance of the second end (adjacent the middle segment of the elongate member) of such one of the segments to the other segment, the bend forms a bent end of the device, in contrast with an end (i.e., a free end) of the elongate member which is (in such configuration) spaced inwardly from the end of the device (i.e., closer to the middle segment of the elongate member than to the ends of the device). In such configuration, a retention member formed by such bent segment may be considered to be positioned inwardly of the end of the device and towards the middle segment of the elongate member/a middle region of the device.

In some embodiments, the elongate member may include one or more retention features along its length, such as a ridge and/or anchor. Accordingly, anastomosis devices described herein may reduce contact area with a tissue with respect to corresponding traditional devices while nonetheless effectively resisting migration.

Embodiments may include one or more retention members with at least one circumferential loop configured to appose tissue, thereby stably holding an anastomosis device against tissue(s), holding multiple tissue layers together, or both. It will be understood that at least one circumferential loop may be open or closed (e.g., having an open portion of a circumference or completing a closed circumference).

In various examples described herein, anastomosis devices described herein may hold and/or support tissue layer(s) for formation of anastomoses via electrocautery methods. It will be understood that anastomoses across tissues formed by cauterizing methods may be defined by fluid-tight junctions of cauterized tissue. However, layers of tissue may need to be held in apposition for the formation of a cauterized anastomosis across the apposed tissue layers, as well as for subsequent time for the layers of tissue to grow together (e.g., fuse together). Anastomoses supported by devices described herein may thus be supported during their formation and/or the healing of apposed tissue while resisting leakage through the cauterized tissue(s) defining the anastomoses.

It will be further recognized that the presence of foreign objects in a body may elicit an immune response from surrounding tissue, particularly if natural motion of the body contributes to abrasion of the surrounding tissue by the foreign object. As a result, a growth response of the tissue may be triggered, which with some traditional devices may result in an occlusion of the formed anastomosis. Of note, various anastomosis devices described herein may not include a member extending through the formed anastomosis, and/or they may minimize or even eliminate contact of the device with tissue surrounding (e.g., defining the walls of) the passage of the anastomosis. For example, devices may not contact tissue about a full perimeter or circumference of an anastomosis. Devices of the present disclosure thus do not contribute to the same abrasion of tissue defining the anastomosis as traditional medical devices, thereby minimizing tissue ingrowth and minimizing the potential occlusion of the formed anastomosis by such tissue ingrowth.

In accordance with various aspects of the present disclosure, each of the retention members (at each end of an anastomosis device formed in accordance with various principles of the present disclosure) defines or circumscribes or delineates a clamping region along the tissue contacted by the retention member, and optionally including tissue between the opposed retention members (on each end of the anastomosis device). Within the clamping regions, an anastomosis region may be defined as a volume extending along (e.g., parallel to) the middle segment of the elongate member but which is free from interference from the elongate member. The tissue in the anastomosis region (e.g., the volume of tissue extending between the surfaces contacted by the first and second retention members and within the clamping region) may be removed to form the anastomosis. In some embodiments, the middle segment of the anastomosis device is offset from (e.g., does not extend through) a central region of the anastomosis region, and may be considered to extend along or even outside a periphery of the anastomosis region. As such, the anastomosis device holds tissue through which an anastomosis is to be formed without interfering with forming of the anastomosis. In other words, the anastomosis may be formed by removing (e.g., cutting, or coring away) tissue defined (e.g., circumscribed or otherwise delineated) by the device while the device is in place and without the device interfering with tissue removal.

In accordance with various aspects of the present disclosure, an anastomosis device is formed of an elongate member with retention members extending transverse to the longitudinal extent of the anastomosis device to contact tissue across which the anastomosis device extends and through which an anastomosis is formed. A middle segment of the elongate member extends between the retention members. In some embodiments, the middle segment is configured and positioned with respect to the anastomosis so as not to contact tissue surrounding the anastomosis, or to contact only a portion of tissue surrounding the anastomosis. For instance, the middle segment of the elongate member may be formed of a wire with a diameter having a minimal extent relative to the circumference of the anastomosis. The middle segment may remain outside the region of the anastomosis (e.g., not within the cored away section of tissue forming a passage through the tissue). More particularly, the middle segment may extend through tissue surrounding the anastomosis without extending into the open passageway of the anastomosis. However, in some instances, the middle segment may be along the periphery of the anastomosis. Even if the middle segment contacts the tissue wall of the anastomosis, such contact is significantly less than contact by tubular anastomosis devices of the prior art. Even so, it is presently contemplated that elongate members may be selected based on their diameters corresponding with a stiffness of the elongate member, which may, for example, relate to a retentive strength of retention members formed thereof. In some embodiments, the diameter of an elongated element forming an anastomosis device in accordance with various principles of the present disclosure may be as small as approximately 0.01" (0.254 mm) and even as small as approximately 0.05" (1.27 mm), including increments of 0.001" (0.0254 mm) therebetween. In some embodiments, the diameter of an elongated element forming an anastomosis device in accordance with various principles of the present disclosure may be as large as approximately 0.075" (1.91 mm), which, although considered relatively thick for a device such as described herein, would be negligible relative to the circumference of the anastomosis and would not result in a detectable obstruction of the anastomosis.

Additionally, or alternatively, devices of the present disclosure may be simple and/or efficient to manufacture, presenting additional benefit(s) over traditional devices.

In some examples described herein, an anastomosis device may comprise one or more retention members formed by bent segments of an elongate body. In some embodiments, at least one retention member may be formed by a wire bent to extend towards apposed tissue, which may increase a retentive strength of the retention member above corresponding retention member designs. In various examples, bent back designs of retention members may include at least one bent back end, which may include a loop (or hook, or fold, or the like) which may be grasped and pulled (i.e., via a grasping element) for removal of the anastomosis device from tissue.

It will be appreciated that although reference is made herein to a device for an anastomosis, and/or formation of an anastomosis, principles of the present disclosure may be applied more broadly. For instance, an anastomosis may generally be considered to be formed between two apposed tissues. However, various principles of the present disclosure may be applied to a single layer of tissue. For instance, a device formed in accordance with various principles of the present disclosure may be used to facilitate formation of a port or passage through tissue, such as by the retention members of the device defining (e.g., circumscribing or delineating) the region of tissue to be cored (e.g., removed). Moreover, principles of the present disclosure may be applied to apposition of tissue through which an anastomosis is not formed.

Figure 1B:
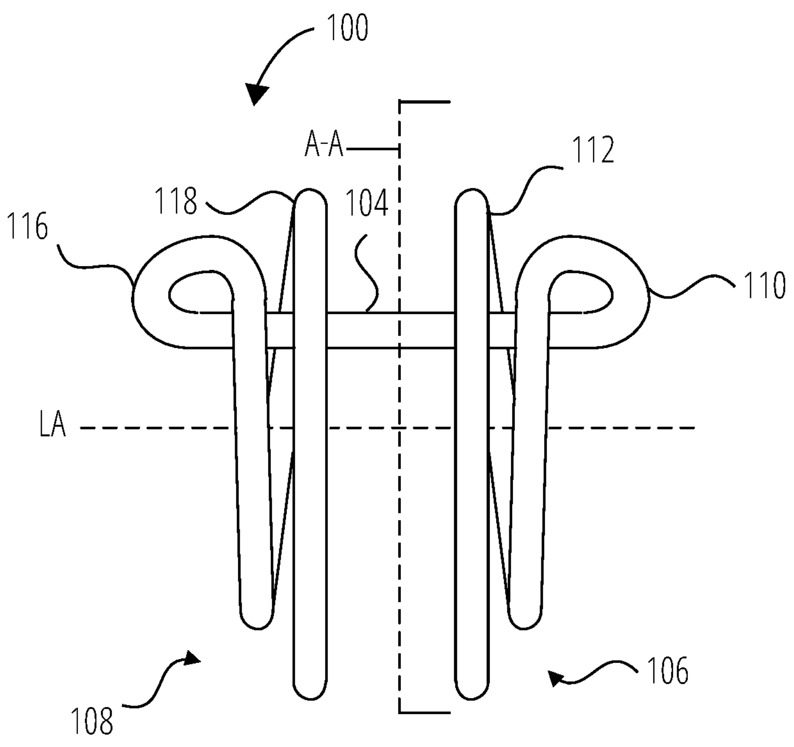
FIG. 1B illustrates a side view of anastomosis device according to one or more embodiments described herein.
Figure 1C:
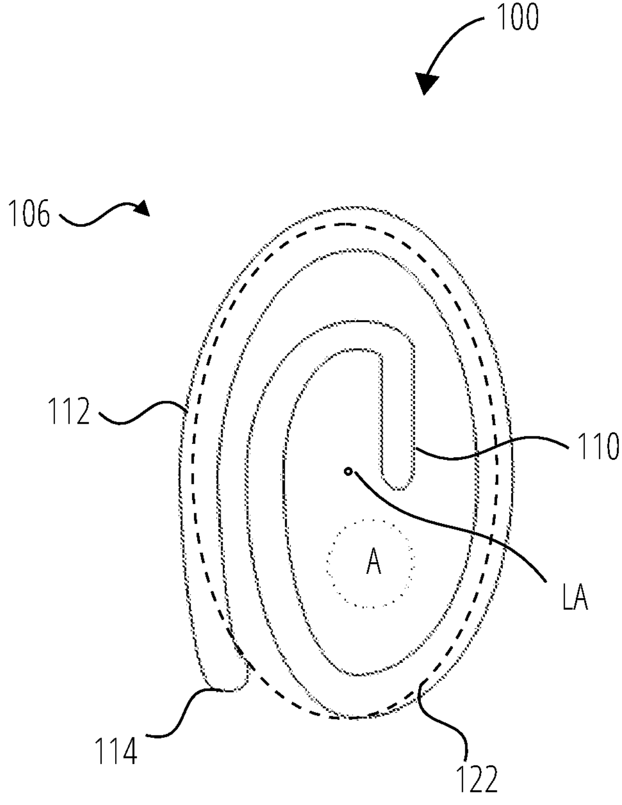
FIG. 1C illustrates an end view of an anastomosis device according to one or more embodiments described herein.

Turning now to the examples of embodiments illustrated in the drawings, and referring first to the example of FIGS. 1A-1C, an anastomosis device 100 may be formed from an elongate element such as a wire 102 or other thin or narrow element with a minimized cross-section, the elongate element having a first delivery configuration and a second deployed configuration. FIGS. 1A-1C illustrate anastomosis device 100 in an example of a deployed configuration. FIG. 1A shows an orthogonal view of anastomosis device 100, FIG. 1B shows a side view of anastomosis device 100, and FIG. 1C shows an end view of anastomosis device 100.

Figure 2A:
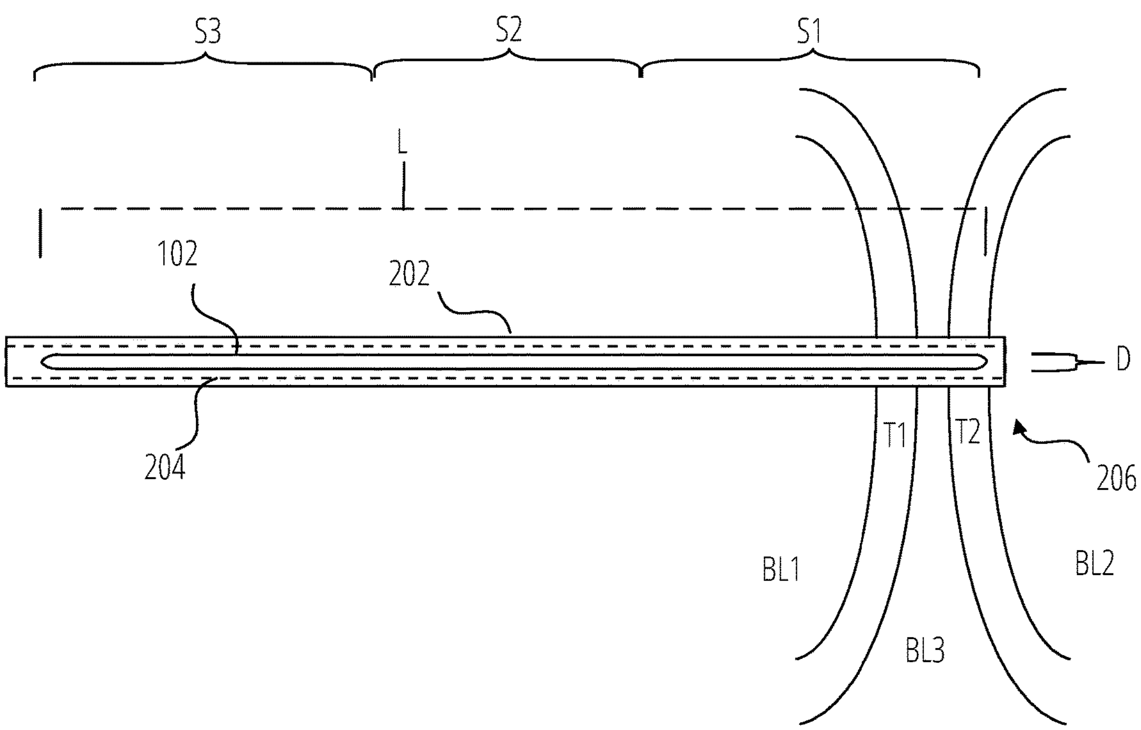
FIG. 2A illustrates an example of delivery of an anastomosis device according to one or more embodiments described herein.

Wire 102 may be formed from a shape memory material, such as nitinol, a shape memory polymer, or the like. In many embodiments, wire 102 may comprise a solid and/or single wire such as is illustrated in FIG. 2A. In various embodiments, anastomosis devices according to the present disclosure may alternatively or additionally be formed from element(s)/elongate member(s) other than a wire. However, for the sake of simplicity, description with respect to anastomosis device 100 may refer to a forming body as wire 102.

Various embodiments of wire 102 include a first segment (e.g., segment "SP"), a second segment (e.g., segment "S3"), and a middle segment 104 extending therebetween (e.g., segment "S2"). Middle segment 104 may be considered a bridging segment, or the like, configured to extend through one or more tissues. While middle segment 104 may be described and illustrated herein as being straight or substantially straight, it will be understood that middle segment 104 may, in various embodiments, additionally or alternatively comprise at least one curve, undulation, or the like. Middle segment 104 may be configured to extend transversely (as used herein, perpendicular or otherwise, and generally greater than 0°) through a plane (not shown for the sake of simplicity) tangent to a location along a tissue. Embodiments are not limited in this context.

At at least one end of middle segment 104, anastomosis device 100 may comprise a retention structure such as first retention member 106 and/or second retention member 108. First retention member 106 may be formed from a bent portion of first segment S1 of wire 102 in the deployed configuration. Similarly, second retention member 108 may be formed with a bent portion of second segment S3 of wire 102 in the deployed configuration. First retention member 106 and/or second retention member 108 may extend transverse to a longitudinal axis LA of anastomosis device 100, such as to contact a surface of tissue through which middle segment 104 of anastomosis device 100 extends.

In various embodiments, wire 102 may bend to form a bent back end 110, 116 of anastomosis device 100, positioning a respective retention member 106, 108 inwardly of the ends 110, 116 of anastomosis device 100 and towards the opposite end segment from which such retention member extends. In other words, and more particularly, in such embodiment, first segment S1 bends towards second segment S3 to form bent back end 110 and retention member 106, with the distance between retention member 106 and second segment S3 being shorter than the distance between bend back end 110 and second segment S3. Similarly, in such embodiment, second segment S3 bends towards first segment 103 to form bent back end 116 and retention member 108, with the distance between retention member 108 and first segment S1 being shorter than the distance between bend back end 116 and first segment S1. When deployed in tissue, such as shown, for example, in FIG. 2C, first bent back end 110 may comprise a bent segment of wire 102 which extends back towards apposed tissue (i.e., tissue layer "T2" of FIG. 2C) and/or middle segment 104. Second bent back end 116 may similarly comprise a bent segment of wire 102 which extends back towards apposed tissue (i.e., tissue layer "T1" of FIG. 2D) and/or middle segment 104. It will be understood that a bent back end may improve a retentive force of anastomosis device 100 by countering lateral forces applied to a respective retention structure by an apposed tissue. In several embodiments, first bent back end 110 and/or second bent back ends 116 may form a device end of anastomosis device 100 (i.e., be the furthest longitudinally extending region or end of the device).

In accordance with various principles of the present disclosure, wire 102 may be bent into a segment extending transversely with respect to a plane in which middle segment 104 resides as a retention member. In other words, at least a portion of S1 and/or S3 may be bent as a retention member residing in a plane intersected by the middle segment 104, with the middle segment 104 being orthogonal or otherwise transverse to the plane in which the retention member (or at least a majority thereof) resides. In various examples, a transversely extending wire segment S1, S2 may extend radially away from middle segment 104 and then may extend around middle segment 104 to form a loop 112 about middle segment 104. It will be understood that the extension may or may not be circular, spiraling, ovular, or the like, and/or may comprise one or more angles, undulations, or the like. In many cases, a portion of the transversely extending wire may be configured to contact apposed tissue about a perimeter wider than a diameter of the middle segment 104 (not shown for the sake of simplicity). Such a wire extending about a perimeter is referred to herein as a "circumferential loop" for the sake of simplicity and without intent to limit. For example, first segment S1 of wire 102 may be bent into first circumferential loop 112, which may be configured to appose a tissue layer and thereby stabilize anastomosis device 100 with respect to the tissue layer (such see, e.g., anastomosis device 100 with respect to tissue layer T2 as illustrated in FIG. 2C). While at least one circumferential loop is illustrated for the sake of clarity in the drawings, it will be understood that additional circumferential loops (e.g., two or more concentric loops) may be additionally helpful in holding anastomosis device 100 with respect to apposed tissue. For example, further radially outward extending loops may spiral and/or concentrically extend laterally outward. As may be seen with respect to FIG. 1C, at least one circumferential loop of a retention member may extend radially outward from and circumferentially around a longitudinal axis LA which extends longitudinally through anastomosis device 100. First circumferential loop 112 and second circumferential loop 118 may define a clamping region 122 with a boundary circumscribed by the loop 112 and/or circumferential loop 118. Clamping region 122 may comprise a volume extending through apposed tissue secured via the contact of the at least one circumferential loop against the tissue. For example, volume between first and second retention members 106, 108 may be defined as clamping region 122 such that an outer wall of clamping region 122 extends between perimeters of first and second retention members 106, 108, as is illustrated in FIG. 2E. It will be further understood that additional concentric loops may widen clamping region 122 and/or increase a pressure on tissue apposed within clamping region 122, and/or may accommodate a non-flat and/or motile surface of apposed tissue. In various embodiments, tissues held in apposition by pressure from anastomosis device 100 within clamping region 122 may fuse over time, enabling subsequent removal of anastomosis device 100 without detriment to an anastomosis or port formed therewithin, as is described with respect to FIGS. 2E-2F.

As can be seen in FIGS. 1A-1C, in some embodiments, longitudinal axis LA may extend through a center point or at least a central region of at least one circumferential loop 112, 118. Circumferential loops 112, 118 may be ovular (as shown in FIG. 1C), or they may be another shape, such as circular, polygonal, undulating, or the like (not shown for the sake of brevity). In many embodiments, middle segment 104 may be offset from (e.g., laterally spaced from, not coaxial, or not coextensive with) longitudinal axis LA.

At any rate, as can be seen in FIG. 1C, the at least one circumferential loop 112, 118 may extend around (e.g., circumscribe) an anastomosis region A smaller than clamping region 122 of tissue(s) between first and second circumferential loops 112, 118. and/or a treatment site, which in many examples is not intersected by middle segment 104 (i.e., in many examples, middle segment 104 does not extend through anastomosis region A). In various embodiments, anastomosis region A resides within clamping region 122 but is unimpeded and/or not intercepted by any part of the elongate body used to form anastomosis device 100. It will be understood that, once anastomosis device 100 is deployed through the treatment site, a tool or instrument such as a cutting element (e.g., an electrocautery tip) may be used to excise or remove or core tissue from within anastomosis region A so as to form an anastomosis. It will be understood that the off-centering of middle segment 104 from longitudinal axis LA and/or the oblong shape of circumferential loops 112, 118 (i.e, not centered within clamping region 122) may provide a larger working space of anastomosis region A (i.e., area within clamping region 122 which is not covered and/or intersected by bend(s) of wire 102) without interference from the middle segment 104. In many embodiments, the off-centering of middle segment 104 and/or an inner diameter of the at least one or more circumferential loops 112, 118 may be configured such that anastomosis region A is sufficiently wide enough to pass a cutting device (e.g., cutting element 210 as described with respect to FIG. 2E) therethrough to form the anastomosis without interference of middle segment 104.

First circumferential loop 112 may end in a first wire end 114 (a first "free" end), and second circumferential loop 118 may end in a second wire end 120 (a second "free" end). Wire ends 114, 120 may be rounded (i.e., domed, convexly curved), as illustrated, or may be squared, pointed, or shaped otherwise. Wire ends 114, 120 may have a same diameter as the rest of wire 102 or a different diameter. In some embodiments, wire ends 114, 120 may be configured to extend substantially parallel to a plane A-A along and transverse or orthogonal to middle segment 104 and/or along an apposed tissue. In other embodiments, wire ends 114, 120 may extend towards plane A-A, which may cause them to interface with, and optionally to anchor into, an apposed tissue (not shown).

Similarly, the at least one circumferential loop 112, 118 may be configured to lie in a plane substantially parallel to plane A-A or to extend towards middle segment 104 at a transverse angle with respect to plane A-A. In some embodiments, at least one of circumferential loops 112, 118 may be in the form of a spiraling wire retention member with loops extending progressively closer to middle segment 104. Without wishing to be bound by any theory, it is believed that a circumferential loop 112, 118 and/or wire end 114, 120 which extends transversely towards plane A-A may increase a retentive strength of anastomosis device 100 above alternative designs by opposing lateral forces exerted on the respective retention member 106, 108 by an apposed tissue.

FIGS. 2A-2D illustrate, by way of example, aspects of a delivery method for a medical device as described herein.

As is shown in FIG. 2A, anastomosis device 100 as disclosed herein may be disposed in a delivery configuration (e.g., unexpanded configuration, straightened configuration, constrained configuration, or the like) within a sheath 202 (e.g., tissue penetrating element, catheter, or the like) defining a lumen 204 extending longitudinally therethrough. In various embodiments, in the delivery configuration, wire 102 may be elongated such that one or more retention member 106, 108, and/or bent back end 110, 116 may be substantially or entirely straightened such that wire 102 is substantially or entirely straight. For example, first retention member 106 may be straightened into segment 51 (e.g., first segment), middle segment 104 may be segment S2, and second retention member 108 may be straightened into segment S3 (e.g., second segment) of wire 102 in a constrained configuration, with segments 51, S2, and S3 generally corresponding to those described with respect to FIG. 1A for the sake of conciseness and without intent to limit. In other words, a length "L" of anastomosis device 100 in a delivery configuration may be the same length L of wire 102 used to form anastomosis device 100. A diameter "D" of anastomosis device 100 in a delivery configuration may be the same or substantially the same as diameter D of wire 102 used to form anastomosis device 100. In many embodiments, positioning of wire 102 within lumen 204 may be sufficient to maintain a straight configuration of wire 102. For example, sheath 202 and/or lumen 204 may comprise a small enough diameter to hold wire 102 in a substantially straight configuration while the wire 102 is disposed within lumen 204. It will be recognized that lumen 204 may thus have a diameter substantially the same size as or only slightly larger than diameter D, which may be smaller than in traditional devices.

Distal end 206 of sheath 202 may be distally advanced from a first body lumen BL1, through first tissue layer T1 and second tissue layer T2, and into second body lumen BL2. Distal end 206 may be directly advanced through tissue layers T1 and T2, or a hole may be formed upon or prior to the advancement, for example, by an electrocautery tip (not shown). In some embodiments, at least one additional body lumen BL3 may reside between tissue layers T1 and T2.

Figure 2B:
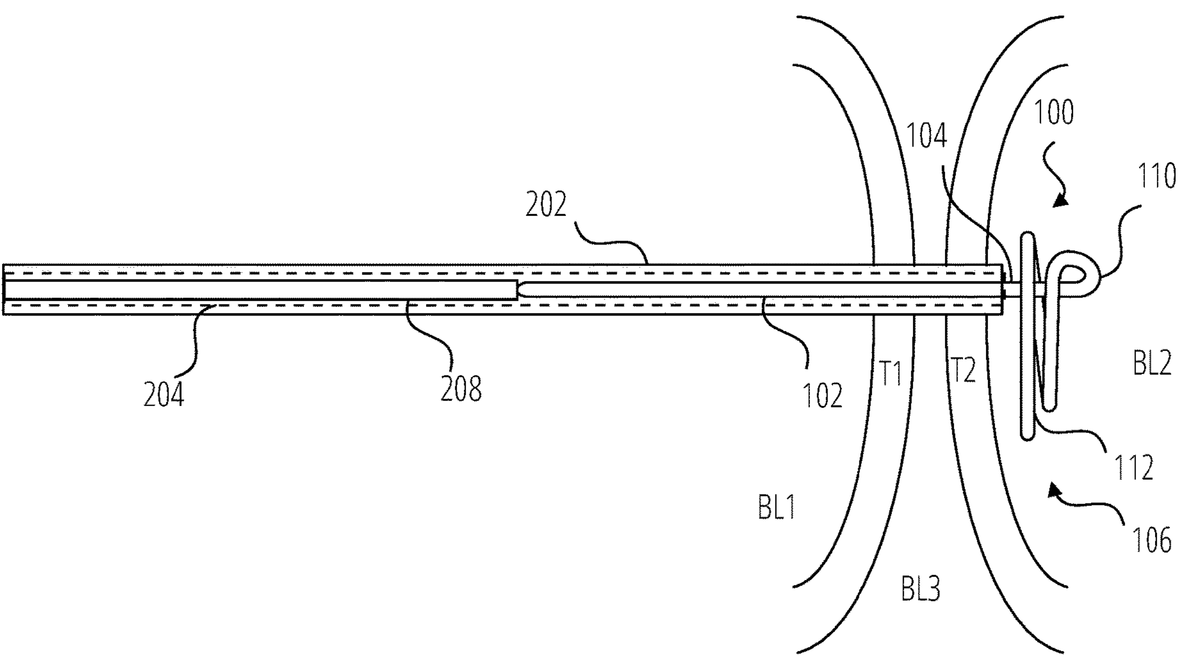
FIG. 2B illustrates an example of an additional step of delivering an anastomosis device according to one or more embodiments described herein.
Figure 2C:
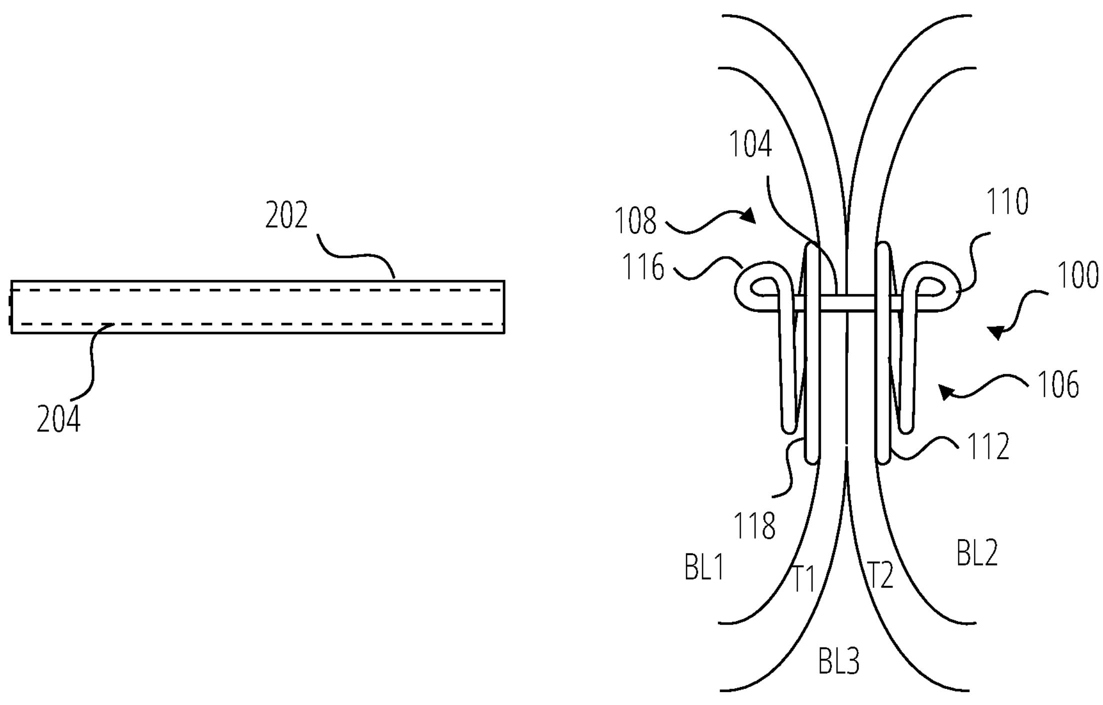
FIG. 2C illustrates an anastomosis device deployed in tissue according to one or more embodiments described herein.

Attention may now be directed to FIG. 2B.

With distal end 206 of sheath 202 advanced through second tissue layer T2, the sheath 202 may be proximally retracted with respect to wire 102 or the wire 102 may be distally extended with respect to sheath 202 (i.e., by applied pressure of a pusher 208, which may be adjacent to and/or coupled to wire 102 within lumen 204), thereby allowing a distal end of wire 102 to move from the delivery configuration to a deployed configuration (i.e., unconstrained configuration, expanded configuration, bent configuration, curled configuration, retentive configuration, or the like, which terms may be used interchangeably and without intent to limit). In particular, the distal end (i.e., segment S1) of wire 102 may transition into first retention member 106 within second body lumen BL2.

In the event that first retention member 106 is not contacting second tissue layer T2, anastomosis device 100 may be proximally retracted with sheath 202 such that first retention member 106 apposes second tissue layer T2. For example, if pusher 208 is coupled to wire 102 (e.g., if pusher 208 includes a grasper), anastomosis device 100 may be proximally retracted with pusher 208, which may be positioned within lumen 204 of sheath 202.

Sheath 202 may then be further proximally retracted through tissue layers T2 and T1 such that first retention member 106 remains in second body lumen BL2 but middle segment 104 (i.e., segment S2) extends through tissue layers T1 and T2.

As can be seen in FIG. 2C, second retention member 108 may then be deployed within first body lumen BL1 by further proximally retracting sheath 202 beyond a proximal end of segment S3 such that S3 forms second retention member 108 by moving to the second configuration. In some embodiments, deployment of second retention member 108 may allow second retention member 108 to press or draw tissue layers T1 and T2 together, for example, bridging additional body lumen BL3 or space between tissue layers T1 and T2 and/or decreasing a distance between tissue layers T1 and T2.

Figure 2D:
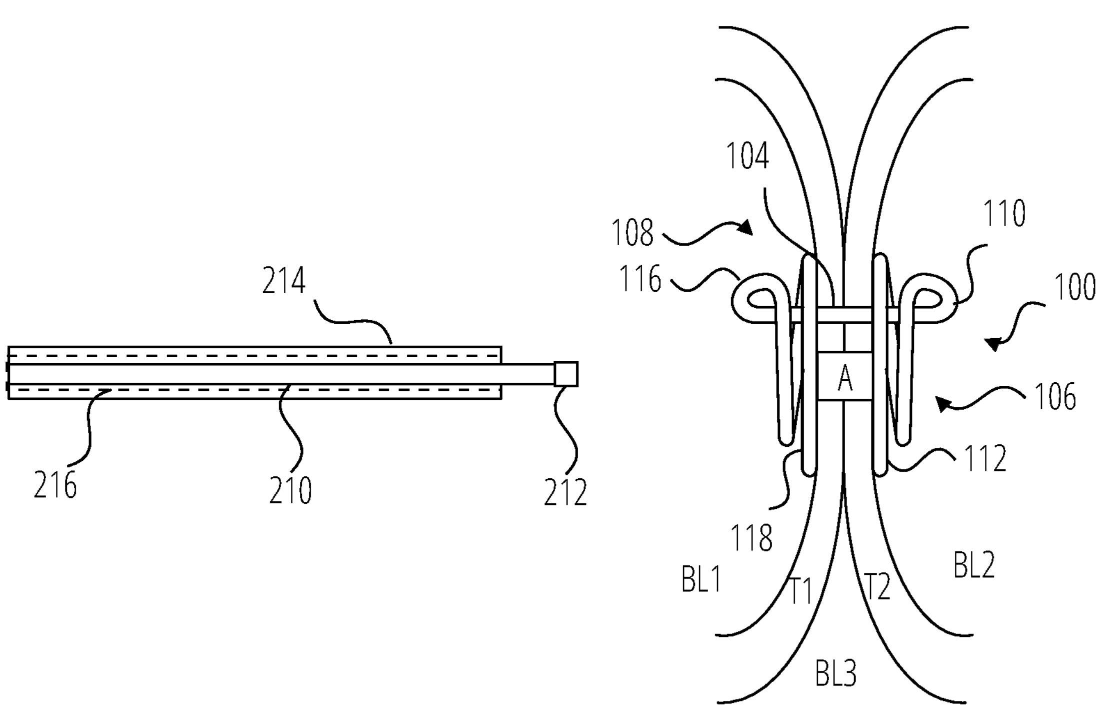
FIG. 2D illustrates an example of creating an anastomosis according to one or more embodiments described herein.
Figure 2E:
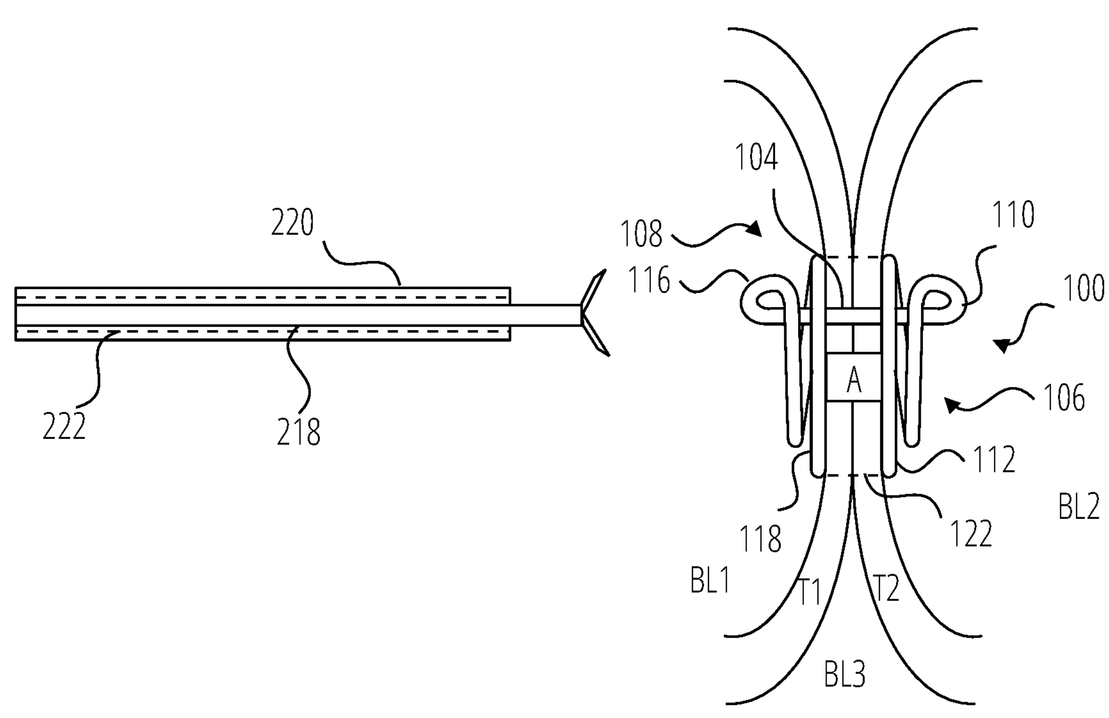
FIG. 2E illustrates an example of positioning an anastomosis device according to one or more embodiments described herein.

Subsequently, a tool such as a cutting element 210, for example, with an electrocautery tip 212, may be aligned with anastomosis region A as illustrated in FIG. 1C and used to create an anastomosis or port at anastomosis region A. In several embodiments, an anastomosis region may coincide with anastomosis region A (i.e., take up a full space available within clamping region 122 which is not interfered or intercepted by the elongate member forming anastomosis device 100 as illustrated in FIG. 2D). In other embodiments, a smaller anastomosis may be created within anastomosis region A. Embodiments are not limited in this context. The formation of the anastomosis may be performed in the same or in a different procedure as the placement of the anastomosis device 100.

Cutting element 210 may be extended through a second sheath 214 defining lumen 216 therethrough, or through the same first sheath 202. For example, pusher 208 may be removed from lumen 204 and replaced with cutting element 210. In another example, cutting element 210 may act as a pusher 208, thereby eliminating a need for a practitioner to change tools during a procedure.

While various types of cutting elements 210 are presently contemplated (i.e., scalpels, needles, scissors, or the like), various embodiments may use electrocautery elements, which, while creating the anastomosis in anastomosis region A, may at the same time burn and/or fuse tissue layers T1 and T2 together. Anastomosis device 100 may thus clamp tissue layers T1 and T2 together and thereby support the maintenance of the anastomosis, for example, as tissue layers T1 and T2 heal, while not itself extending through the conduit of the anastomosis. Without wishing to be bound by any theory, it is believed that presently disclosed devices, systems, and methods may thus allow for healing of an anastomosis without continued aggravation of such by a medical device extending therethrough. It is recognized that middle segment 104 may be the only portion of anastomosis device 100 which actively bridges tissue layers T1 and T2. In embodiments as described herein, in which middle segment 104 is a simple elongate member such as a wire, such configuration of middle segment 104 reduces an area of surface contact and of potential irritation with apposed tissue over traditional anastomosis devices.

In various embodiments, as shown in FIG. 2E, a grasper 218 may be used to adjust a position of and/or remove anastomosis device 100. In particular, grasper 218 may be extended through a sheath 220 defining lumen 222, which may be the same or a different sheath from sheath 202, 214. Grasper 218 may be used to grasp a bent back end 110, 116 of anastomosis device 100, which may allow anastomosis device 100 to be adjusted in position even after deployment.

In some examples, a practitioner may desire to remove anastomosis device 100 from tissue, for example, if the anastomosis of anastomosis region A has healed and/or there is no longer a need for anastomosis device 100 to be implanted. In this case, grasper 218 may hold onto second bent back end 116 and be proximally retracted together with second bent back end 116.

Figure 2F:
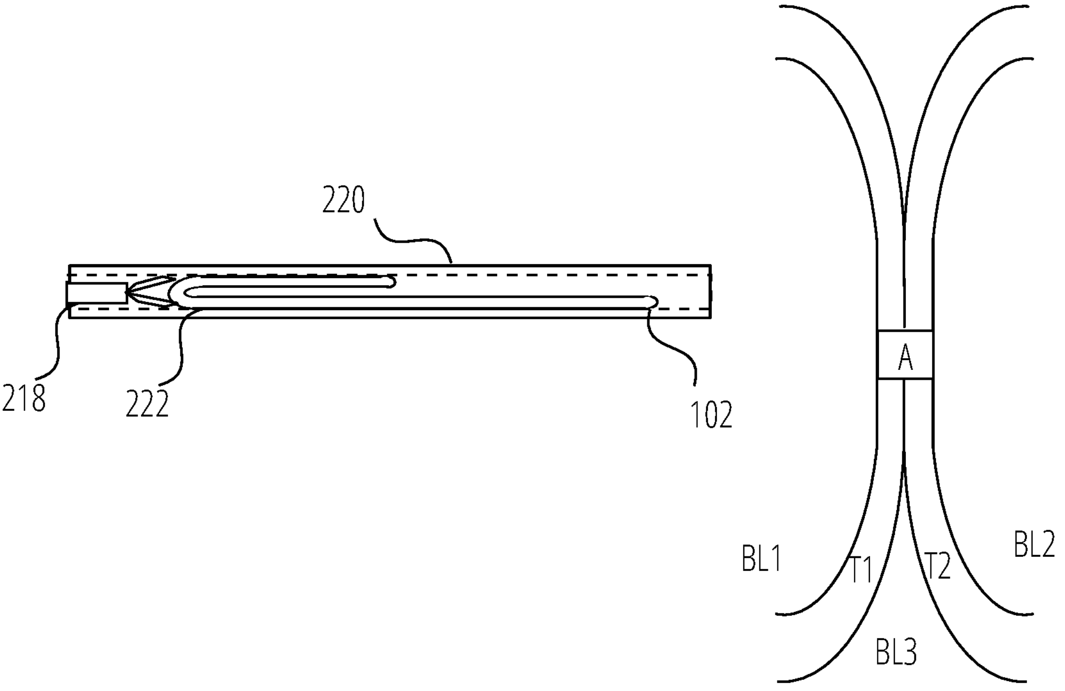
FIG. 2F illustrates an example of removing an anastomosis device according to one or more embodiments described herein.

In response to the applied force to second bent back end 116, wire 102 defining at least first retention member 106 may straighten and slide through tissue layers T2 and T1, thereby allowing removal of the anastomosis device 100 from its deployed position in tissue. For example, the segment S1 of wire 102 forming first circumferential loop 112 may straighten as it is pulled proximally through tissue layers T2 and T1. In some embodiments, grasper 218 may be then further proximally retracted with second bent back end 116 with respect to sheath 220 such that wire 102 is captured within sheath 220 as shown in FIG. 2F. Sheath 220 may then be removed from first body lumen BL1.

In various embodiments of the present disclosure, anastomosis devices may comprise one or more retention features. Retention features may be configured to interface with apposed tissue so as to increase a resistance of an anastomosis device to slide and/or otherwise migrate with respect to the apposed tissue. Retention features may be located selectively along a surface of an element, such as a wire used to form an anastomosis device (i.e., selectively along a portion of wire configured to interface with tissue) or along an entire length of the surface of the element used to form the anastomosis device.

For example, wire 102 used to form anastomosis device 100 may comprise a round wire with a circular cross-sectional surface (not shown). Alternatively, at least a portion of wire 102 may comprise a cross-sectional surface with a non-circular shape. Varied surfaces may comprise one or more retention features along a length of the wire with such cross-sectional surfaces. For example, angled or protruding portions of wire surfaces may serve as retention features which at aid in securing a position of the wire with respect to apposed tissue.

Figure 3:
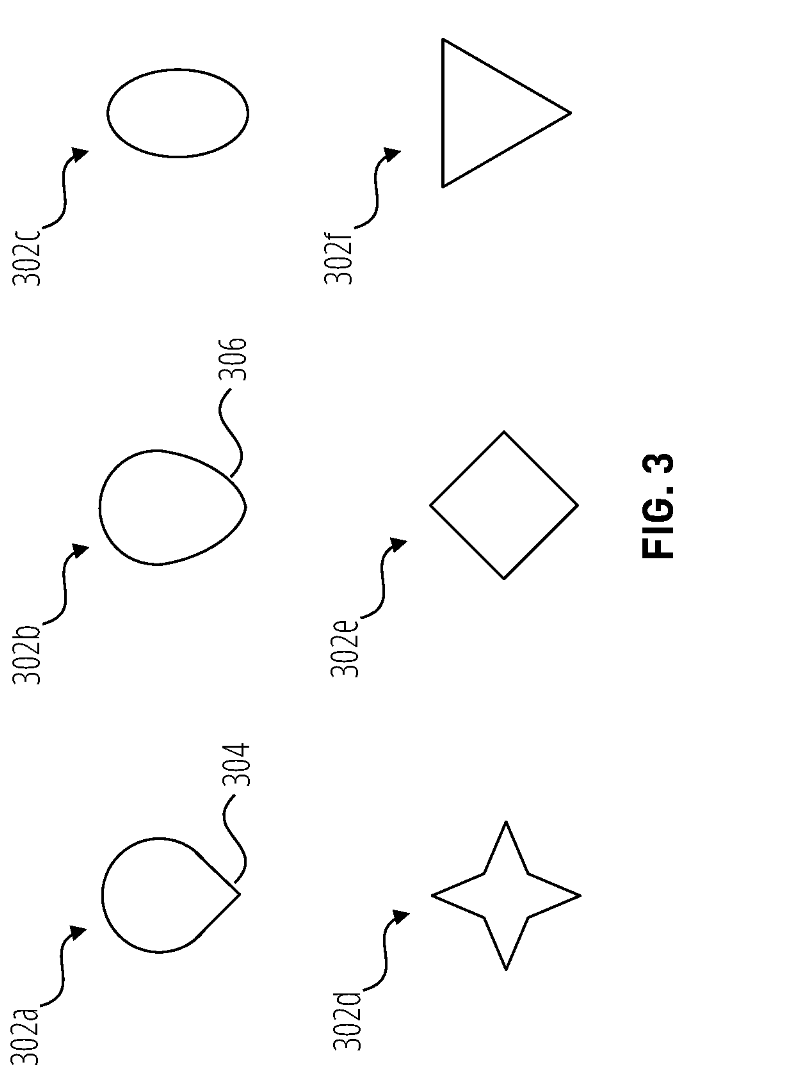
FIG. 3 illustrates various cross-sectional wire profiles according to embodiments described herein.

FIG. 3 illustrates various options of wire cross-sections 302*a-f*, although embodiments are not limited in this context.

For example, wire cross section 302*a* features a surface drawn to a point 304, which may be configured to interface with apposed tissue. In the example of a wire with wire cross section 302*b*, a rounded point 306 with a smaller radius of curvature than at other points about the surface of the wire may present a less traumatic tissue interface as opposed to wire cross section 302*a*, but a more retentive surface than a wire with a corresponding circular cross-section. A wire with wire cross section 302*c* may be oblong. In various other embodiments, a wire may have a cross-section with a starred shape (wire cross section 302*d*), a squared or rectangular shape (wire cross section 302*e*), a triangular shape (wire cross section 302*f*), and/or other polygonal or irregular or angled or not-completely-rounded or non-rounded cross-section.

Retention features (i.e., wire surface features) with cross-sections as described with respect to FIG. 3 may extend fully or partially along length L of wire 102, as illustrated in FIG. 2A. In some embodiments, cross-sections as discussed with respect to FIG. 3 may extend uniformly along a wire, or they may linearly extend circumferentially about an axis extending through the wire (not shown). Various portions of a wire may comprise the same or different cross-sectional profiles. Embodiments are not limited in this context.

Figure 4:
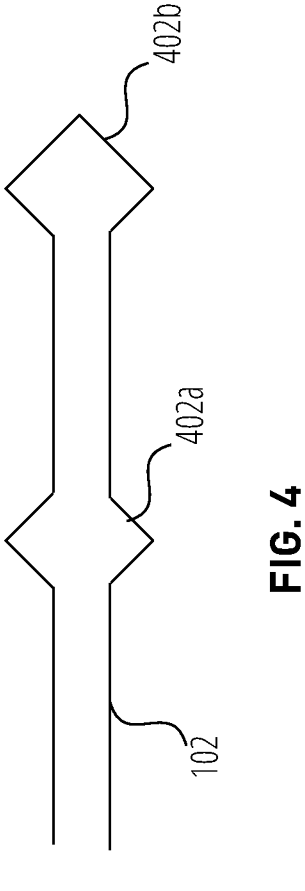
FIG. 4 illustrates a wire, such as may be used to form an anastomosis device, comprising one or more anchoring features according to various embodiments described herein.

In some embodiments, a wire forming anastomosis device 100 may comprise one or more anchors along its length L, wherein the one or anchors comprise the profiles illustrated in FIG. 3. For example, in FIG. 4, anchors 402*a*, 402*b* comprise the profile illustrated as wire cross-section 302*e*. Anchor 402*a* is disposed along wire 102, whereas anchor 402*b* is disposed at an end of wire 102, such as at first wire end 114 or second wire end 120. Examples of embodiments may include one or multiple anchors (i.e., anchoring features) disposed at regular or irregular intervals along the length L of wire 102. In some embodiments, wire 102 may only include a non-circular cross-section and/or at least one anchoring feature along a retention member 106, 108, for example, in order to minimize unwanted abrasion to surrounding tissue. In other embodiments, wire 102 may comprise a non-circular cross-section and/or at least one anchoring feature anywhere along its length L, which may, for example, reduce complexity of manufacturing anastomosis device 100.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The following claims are hereby incorporated into this Detailed Description by this reference, with each claim standing on its own as a separate embodiment of the present disclosure. In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous. In addition, singular references do not exclude a plurality. Reference signs in the claims are provided merely as a clarifying example and shall not be construed as limiting the scope of the claims in any way.

What is claimed is:

1. A device, comprising:

an elongate member comprising a first segment, a second segment, and a middle segment extending therebetween;

wherein:

the elongate member is configured to move between a first configuration and a second configuration;

in the second configuration:

each of the first segment and the second segment extends towards the middle segment to form a respective first bent back end and second bent back end of the device and to form a first retention member with a perimeter circumscribing a clamping region and positioned between the middle segment and the first bent back end, and a second retention member with a perimeter circumscribing the clamping region and positioned between the middle segment and the second bent back end;

at least one of the bent back ends forms an axially-extending loop configured to be grasped and pulled for removal of the device from tissue; and the middle segment extends through the clamping region, offset from a central axis of the clamping region to extend along a periphery of the clamping region radially inwardly from the perimeter of the retention members with the axially-extending loop extending radially away from and offset from the central axis between the middle segment and the periphery of the clamping region, with the middle segment positioned radially between the central axis and the axially-extending loop.

2. The device of claim 1, wherein the elongate member in the first configuration is substantially straight, with the first and second segments extending substantially coaxially from the middle segment.

3. The device of claim 1, wherein each of the first segment and the second segment forms the respective bent back ends of the device along a portion of the elongate member between the middle segment of the elongate member and the respective retention member.

4. The device of claim 1, wherein the elongate member has a non-circular cross section.

5. The device of claim 1, wherein each of the first segment and the second segment extends to form one or more loops.

6. The device of claim 1, wherein the retention members are configured to appose respective first and second tissue layers through which the middle segment extends.

7. The device of claim 1, wherein the retention members are configured to draw the first and second tissue layers into apposition.

8. The device of claim 1, wherein the retention members form one or more circumferentially-extending loops configured to circumscribe an anastomosis region.

9. The device of claim 8, wherein the middle segment does not intersect a central region of the anastomosis region.

10. An anastomosis device, comprising:

an elongate member configured to transition between a first configuration and a second configuration, wherein:

in the first configuration, the elongate member is substantially straight;

in the second configuration:

the elongate member forms a first retention member and a second retention member with a middle segment extending therebetween;

the middle segment extends through an area circumscribed by and radially inward of a perimeter defined by the first and second retention members, and is offset from a central axis of the elongate member so that the area circumscribed by the first and second retention members has a diameter sized for and enabling excision of tissue extending longitudinally therethrough without interference of the middle segment to create a port extending through the anastomosis device; and the elongate member forms a first bent back end radially between the middle segment and the perimeter defined by the first retention member, and radially offset from the central axis in the same direction that the middle segment is offset from the central axis.

11. The anastomosis device of claim 10, wherein the first retention member and the second retention member are configured to appose first and second tissue layers.

12. The anastomosis device of claim 11, wherein the first and second retention members are configured to draw the first and second tissue layers into apposition.

13. The anastomosis device of claim 10, wherein the first retention member, the second retention member, or both comprise one or more circumferential loops.

14. The anastomosis device of claim 13, wherein the middle segment is configured not to extend through a central region of the anastomosis region.

15. The anastomosis device of any of claim 10, wherein in the second configuration, the elongate member forms a second bent back end radially between the middle segment and the second retention member.

16. The anastomosis device of claim 10, wherein the elongate member has a non-circular cross section.

17. The anastomosis device of claim 10, wherein the middle segment is configured not to be centered within a clamping region defined by the first retention member, or the second retention member, or both, and is configured to be outside the anastomosis region.

* * * * *